(12) United States Patent
Hall et al.

(10) Patent No.: US 10,206,548 B1
(45) Date of Patent: *Feb. 19, 2019

(54) DOPED AND NON-DOPED TITANIUM DIOXIDE COATED ANTIMICROBIAL TOILET

(71) Applicants: David R. Hall, Provo, UT (US); Steven J. M. Butala, Provo, UT (US); Ben Swenson, Lehi, UT (US); Joe Fox, Spanish Fox, UT (US)

(72) Inventors: David R. Hall, Provo, UT (US); Steven J. M. Butala, Provo, UT (US); Ben Swenson, Lehi, UT (US); Joe Fox, Spanish Fox, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/678,461

(22) Filed: Aug. 16, 2017

(51) Int. Cl.
*A47K 13/14* (2006.01)
*A47K 13/24* (2006.01)
(Continued)

(52) U.S. Cl.
CPC .............. *A47K 13/24* (2013.01); *A61L 2/088* (2013.01); *A61L 2/10* (2013.01); *A61L 2/24* (2013.01); *B01J 21/063* (2013.01); *B01J 23/50* (2013.01); *B01J 27/02* (2013.01); *B01J 27/135* (2013.01); *B01J 27/18* (2013.01); *B01J 27/20* (2013.01); *B01J 27/24* (2013.01); *B01J 35/004* (2013.01); *B01J 35/0006* (2013.01); *E03D 5/092* (2013.01); *E03D 9/005* (2013.01); *E03D 11/13* (2013.01); *A61L 2202/11* (2013.01)

(58) Field of Classification Search
CPC ..................................................... A47K 13/24

USPC ....................................................... 4/222, 233
See application file for complete search history.

(56) References Cited

U.S. PATENT DOCUMENTS

| 2,460,543 A | * | 2/1949 | Spierer | ................ | A47K 13/302 4/233 |
| 2008/0134420 A1 | * | 6/2008 | Ho | ........................ | A47K 13/302 4/233 |

(Continued)

FOREIGN PATENT DOCUMENTS

| CN | 102527363 A | * | 7/2012 |
| JP | 2009066594 A | * | 4/2009 |

OTHER PUBLICATIONS

JP 2009-066594 A Derwent English abstract dated Mar. 28, 2018.*
(Continued)

*Primary Examiner* — Christine Skubinna

(57) ABSTRACT

An antimicrobial toilet includes an inner surface of a toilet bowl which includes a non-doped titanium dioxide coating. The titanium dioxide coating is photocatalytic and antimicrobial in the presence of ultraviolet (UV) light. In the absence of UV light, the inner surface of the toilet bowl is not antimicrobial. The UV light source may be actuated after the waste has exited the toilet bowl. Consequently, the waste may be used in digesters used to produce clean energy or for analysis to assess the user's health status without being exposed to the antimicrobial properties of the titanium dioxide coating. The UV light may then be actuated to disinfect the toilet bowl. The outer shell of the toilet is coated with a doped titanium dioxide. The doped titanium dioxide is photocatalytic and antimicrobial in the presence of visible light. The outer shell is antimicrobial when standard room lights are actuated.

15 Claims, 6 Drawing Sheets

(51) Int. Cl.
*E03D 5/092* (2006.01)
*E03D 9/00* (2006.01)
*E03D 11/13* (2006.01)
*A61L 2/08* (2006.01)
*A61L 2/10* (2006.01)
*A61L 2/24* (2006.01)
*B01J 21/06* (2006.01)
*B01J 27/24* (2006.01)
*B01J 27/20* (2006.01)
*B01J 27/18* (2006.01)
*B01J 27/02* (2006.01)
*B01J 27/135* (2006.01)
*B01J 23/50* (2006.01)
*B01J 35/00* (2006.01)

(56) References Cited

U.S. PATENT DOCUMENTS

2010/0023492 A1* 1/2010 Lucas ................. A61L 2/10
                                                   220/200
2014/0304903 A1* 10/2014 Cogswell ............. E03D 9/052
                                                   4/314

OTHER PUBLICATIONS

CN 102527363 A Derwent English Abstract dated Mar. 28, 2018.*
PMC Scientific Report Published Feb. 10, 2014 printed Mar. 28, 2018.*

* cited by examiner

DOPED AND NON-DOPED TITANIUM DIOXIDE COATED ANTIMICROBIAL TOILET

FIELD OF THE INVENTION

This disclosure relates to antimicrobial coatings on a toilet.

BACKGROUND OF THE INVENTION

Bathrooms and toilets include surfaces where microbes are deposited and proliferate. These surfaces are continually exposed to additional microbes each time a user enters the bathroom, especially if the user uses the toilet. Consequently, it is impractical to effectively disinfect bathroom and toilet surfaces at a rate which provides a disinfected area for each new user.

While it is important to periodically disinfect a toilet, in some circumstances, it is desirable to delay killing microbes which may be present in a user's excrement. For example, the toilet may be a medical toilet which collects and analyzes the user's urine or feces to provide information that is relevant to the user's health status. In another example, the user's excrement may be transferred to an anaerobic digester to produce biofuel or used as fertilizer. Consequently, control of disinfection of surfaces in the bathroom and on the toilet with regard to time and space are needed.

Titanium dioxide composites subjected to ultraviolet light excitation have been shown to possess effective antimicrobial activity. These composites are effective in eliciting the death of both Gram-positive and Gram-negative bacteria. More recently, doped titanium dioxide composites have been found to be activated by visible light and also to possess antimicrobial activity. The properties of these different titanium dioxide composites and their exposure to light of different wavelengths may be useful to design a toilet or full bathroom that includes antimicrobial surfaces.

BRIEF SUMMARY OF THE INVENTION

The antimicrobial toilet disclosed herein includes a toilet bowl with an inner surface. The inner surface may be coated with a non-doped titanium dioxide composite. The non-doped titanium dioxide composite is photocatalytic and antimicrobial in the presence of ultraviolet (hereinafter, "UV") light.

The antimicrobial toilet may also include a base, an outer surface of a toilet bowl, a seat, a toilet lid, a tank, and flush handle. Collectively, these surfaces may comprise an outer shell of the toilet. The outer surface may be coated with a doped titanium dioxide composite. The doped titanium dioxide composite is photocatalytic and antimicrobial in the presence of visible light. Consequently, by exposing the doped or non-doped titanium dioxide coatings to light of a known wavelength (visible or UV), the antimicrobial properties of the surfaces may be differentially activated. The titanium dioxide particles and the doped-titanium particles may comprise mixed particle sizes ranging between 0.02 and 0.150 micrometers.

The doped titanium dioxide coating may include one or more noble metals, transition metals, and/or non-metals. The doped titanium dioxide coating may be doped with a single doping component or co-doped with two or more doping components.

The visible light source may be a traditional light bulb, or light emitting diode (hereinafter, "LED") light that may be used to illuminate the bathroom in which the toilet is placed. The visible light source may be the same light source that functions to provide light for a user to see when in the user is in the bathroom.

The UV source may be positioned so that it directs UV light toward the inner surface of the toilet bowl. Examples of locations which the UV light source may be placed include embedded in or mounted on a toilet lid. The UV light source may be actuated when the toilet lid is lowered and deactivated when the toilet lid is raised.

In another example, the UV light source includes one or more LED strips which emit UV light. The one or more LED strips may be mounted on the inner surface of the toilet bowl. In some embodiments, the one or more LED strips encircle the circumference of the inner surface of the toilet bowl.

The UV light source may be actuated and deactivated by a switch. The switch may actuate the UV light source after the user's excrement has exited the toilet bowl, for example, after flushing a water toilet. Consequently, the UV light source does not initiate the antimicrobial properties of the non-doped titanium dioxide coating until at least most of the excrement is absent from the toilet. The microbes in the excrement that has left the toilet bowl remain viable and those left behind in the toilet bowl are largely killed.

The switch may be connected to a flush handle causing the UV light to actuate after a flush. In addition, the switch may be connected to a timing device. The timing device may receive a first signal that the flush handle has been actuated causing the toilet to flush. The timing device may be calibrated to send a second signal to the UV light source to actuate the UV light source a defined number of seconds after receiving the first signal. This may provide enough time for the flush to complete before the UV light is actuated.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood regarding the following description and accompanying drawings where.

DETAILED DESCRIPTION OF THE INVENTION

Figure 1:
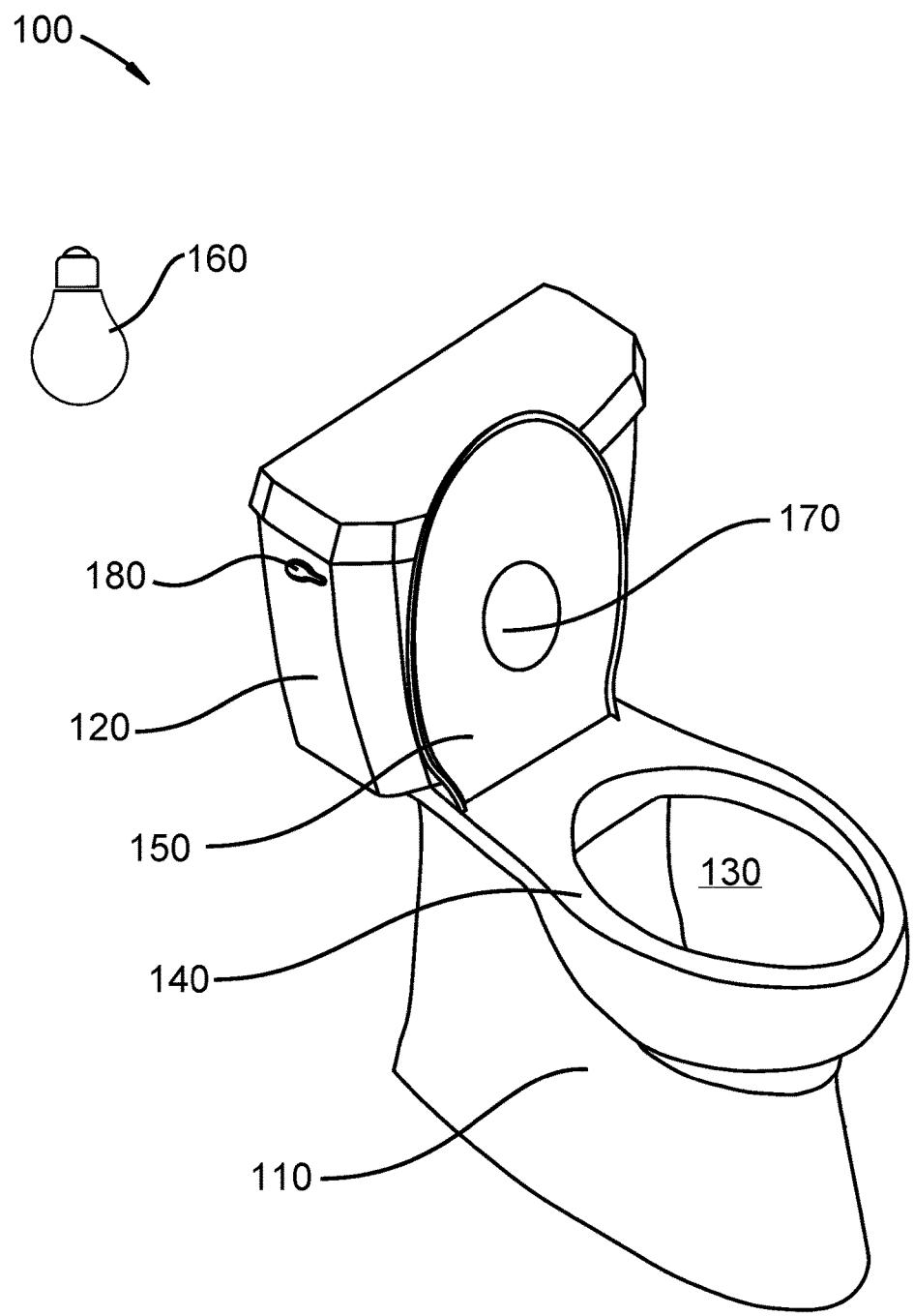
FIG. 1 is a perspective view of an embodiment of a titanium-dioxide coated toilet with the teachings and principles of the disclosure.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a toilet which includes surfaces coated with titanium dioxide composites. The titanium dioxide composites may include one or more of the three different titanium dioxide polymorphs: rutile, anatase and brookite.

The toilet may include one or more of the following: a base, a toilet bowl, a seat, a toilet lid, a tank, and flush handle. The toilet bowl may include an outer surface. The toilet bowl may also include an inner surface which is coated with a UV light activatable titanium dioxide composite. This composite may possess antimicrobial properties when exposed to UV light. The remaining surfaces of the toilet may collectively create an outer shell. The outer shell may be coated with a doped titanium dioxide composite which is activated by visible light. Thus, the doped titanium dioxide composite may be antimicrobial in the presence of visible light. The titanium dioxide particles and the doped titanium dioxide particles may comprise sizes ranging between 0.02 and 0.150 micrometers.

The doped titanium dioxide composite may be doped with a variety of materials. These may include transition metals, including, but not limited to, iron (Fe), copper (Cu), cobalt (Co), nickel (Ni), chromium (Cr), vanadium (V), manganese (Mn), molybdenum (Mo), niobium (Nb), tungsten (W), ruthenium (Ru), platinum (Pt), and gold (Au). In some embodiments, the doped titanium dioxide component may include noble metals. The noble metals used to dope the titanium dioxide as used herein include, but are not limited to, silver (Ag), gold (Au), platinum (Pt), and palladium (Pd). In some embodiments, the titanium dioxide composite may be doped with both transition metals and noble metals.

In some embodiments, the doped titanium dioxide composites may include non-metals. These non-metals may include one or more of carbon, nitrogen, phosphorus, sulfur, and fluorine.

In one embodiment, the doped titanium dioxide composite includes nitrogen according to the following formula: $TiO_{2-x}N_x$.

In one embodiment, the doped titanium dioxide composite includes between about 0.5% and 2.0% nitrogen.

In one embodiment, the doped titanium dioxide composite includes carbon according to the following formula: $C-TiO_2$.

In one embodiment, the doped titanium dioxide composite includes both carbon and nitrogen.

In one embodiment, the doped titanium dioxide composite includes both fluorine and nitrogen.

The antimicrobial toilet may include a UV light source. The UV light source may be positioned in a variety of locations on or within the toilet so as to emit UV light toward the non-doped titanium dioxide composite which coats the inner surface of the toilet bowl. In one embodiment, the UV light source is mounted on or embedded in a toilet lid. When the toilet lid is in a lowered position, the UV light source may be actuated thus emitting UV light into the toilet bowl. When the lid is in a raised position, the UV light source may be deactivated. The deactivation upon raising the toilet lid may provide a safety feature which prevents a user from being exposed to UV light. It may also delay the biocidal activity within the toilet bowl until an action has been performed to cause the excrement to exit the toilet bowl, for example, flushing of a water toilet.

A switch may be connected to the UV light source which actuates the UV light source when the toilet lid is lowered. In one example, the switch is positioned on the toilet lid. When the toilet lid is lowered, the switch comes in contact with the toilet seat. At this point, the switch is between the toilet lid and the toilet seat. The weight of the toilet lid may apply pressure to the switch causing it to actuate. The switch may then be deactivated with the toilet lid is raised.

In another embodiment, the UV light source may be positioned within the toilet bowl. For example, the UV light source may include one or more LED strips. In one embodiment, the one or more LED strips may be positioned on the inner surface of the toilet bowl below a rim of the toilet bowl. In some embodiments, the one or more LED strips may be positioned on the inner surface of the toilet bowl and encircle a circumference of the toilet bowl.

In some embodiments, it may be desirable to actuate the UV light source after the user's excrement has exited the toilet bowl, for example, after flushing a water toilet. This may be accomplished by electrically or mechanically connecting a flush handle to a timing device. The timing device may be calibrated to send a signal to the UV light source a defined amount of time after the flush handle has been actuated. This signal may be transmitted through an electrical connection between the timing device and the UV light source. Consequently, the user may flush the toilet and the timing device may then receive a signal that the flush handle has been actuated. A defined number of seconds after the timing device receives the signal, the timing device may transmit a signal to the UV light source to actuate the UV light source. The UV light may then activate the antimicrobial activity of the titanium dioxide coating on the inner surface of the toilet bowl.

Referring now to the drawings, FIG. 1 illustrates toilet 100 which is a titanium-dioxide coated toilet. Toilet 100 includes base 110, tank 120, and toilet bowl 130. Seat 140 is positioned on top of toilet bowl 130. Lid 150 may be raised and lowered and includes UV light source 170. Flush handle 180 is disposed on tank 120. Visible light source 160 illuminates the toilet and the bathroom where the toilet is positioned. The surfaces of base 110, tank 120, seat 140, lid 150, and flush handle 180 are covered with an outer shell. The outer shell may be coated with doped titanium dioxide which is photocatalytic in the presence of visible light. The inner surface of toilet bowl 130 is coated with a non-doped titanium dioxide which is photocatalytic in the presence of UV light. Consequently, the outer shell of toilet 100 is antimicrobial in the presence of visible light from visible light source 160. Toilet bowl 130 is antimicrobial when UV light source 170 is actuated.

Figure 2A:
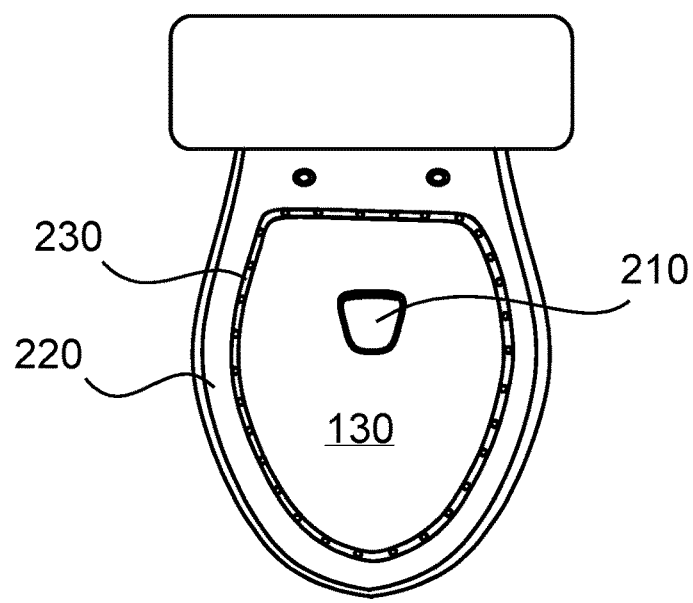
FIG. 2A is an aerial view of an embodiment of a toilet bowl with an ultraviolet light source comprising a light emitting diode strip around the circumference of the inner surface of the toilet bowl with the teachings and principles of the disclosure.
Figure 2B:
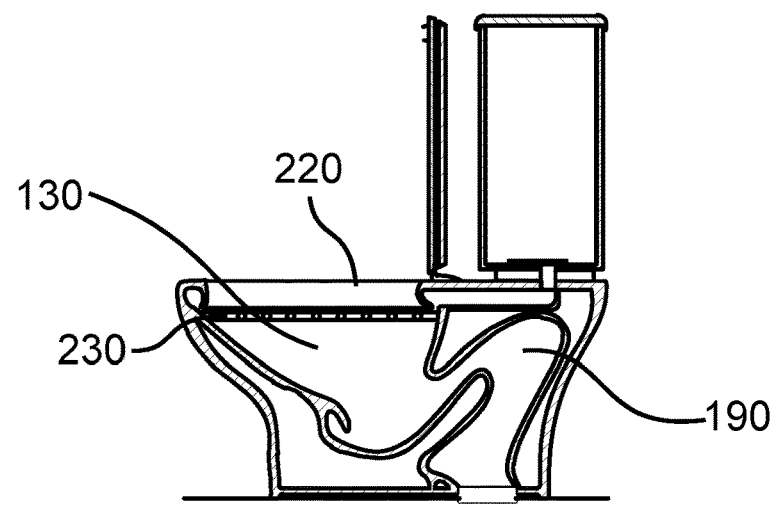
FIG. 2B is a cross-sectional view of the toilet bowl of FIG. 2A.

FIGS. 2A and 2B illustrate another embodiment of a toilet bowl with the teachings and principles of the disclosure. FIG. 2A is an aerial view of toilet bowl 130 which includes orifice 210 which leads to a trap way and rim 220. The UV light source includes light emitting diode (hereinafter, "LED") strip 230. Looking down into toilet bowl 130, LED strip 230 is disposed below rim 220 on the inner surface of toilet bowl 130. LED strip 230 also encircles the circumference of toilet bowl 130. Consequently, when LED strip 230 is actuated, all or most of the inner surface of toilet bowl 130 is exposed to UV light which activates the non-doped titanium dioxide coating.

FIG. 2B is a cross-section of toilet bowl 130 as shown in FIG. 2A. LED strip 230 is shown below rim 220 within toilet bowl 130. Toilet bowl 130 is connected to trapway 190 through which waste travels as it exits toilet bowl 130.

Figure 3A:
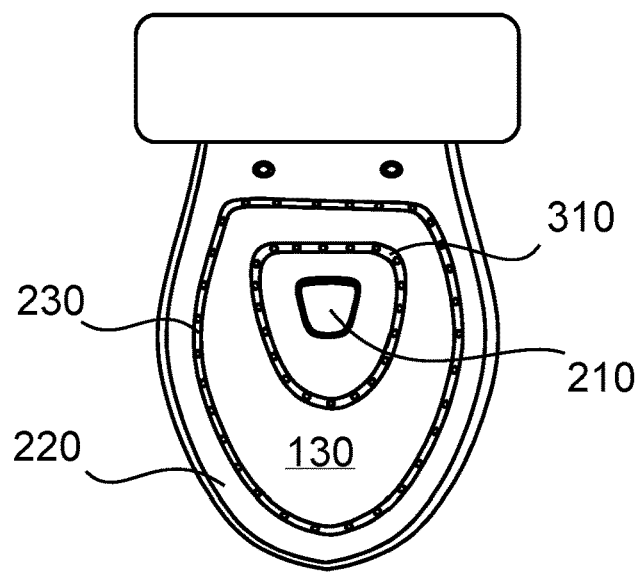
FIG. 3A is an aerial view of an embodiment of a toilet bowl with an ultraviolet light source comprising a plurality of light emitting diode strips around the circumference of the inner surface of the toilet bowl with the teachings and principles of the disclosure.
Figure 3B:
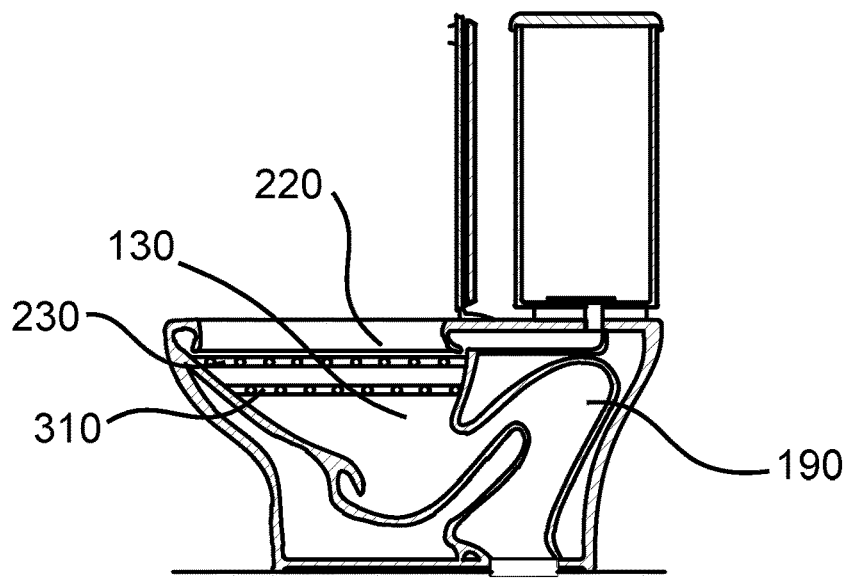
FIG. 3B is a cross-sectional view of the toilet bowl of FIG. 3A.

FIGS. 3A and 3B show another embodiment of a toilet bowl 130 in which the UV light source comprises multiple LED strips placed around the circumference of the inner surface of toilet bowl 130. Similar to the embodiment of FIGS. 2A and 2B, the embodiment shown in FIGS. 3A and 3B includes LED strip 230 below rim 220. In addition, FIGS. 3A and 3B show a second LED strip, LED strip 310, which is positioned below LED strip 230 around the circumference of the inner surface of toilet bowl 130. Consequently, there are two rows of LED strips which emit UV light toward the inner surface of toilet bowl 130 to initiate the antimicrobial properties of the non-doped titanium dioxide coating. Toilet bowl 130 is connected to trapway 190 through which waste travels as it exits toilet bowl 130.

Figure 4A:
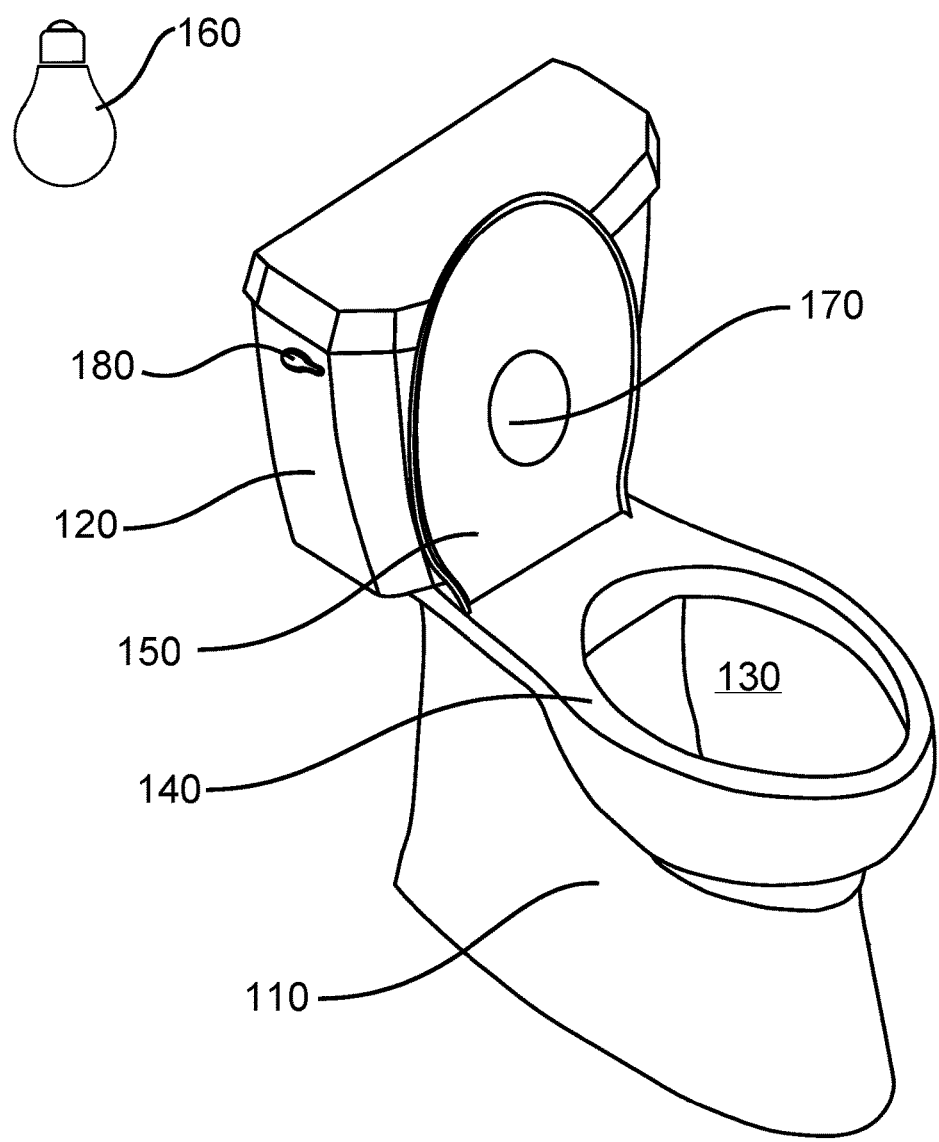
FIG. 4A is a perspective view of an embodiment of a titanium-dioxide coated toilet with the teachings and principles of the disclosure which includes an ultraviolet light source in a raised toilet lid.
Figure 4B:
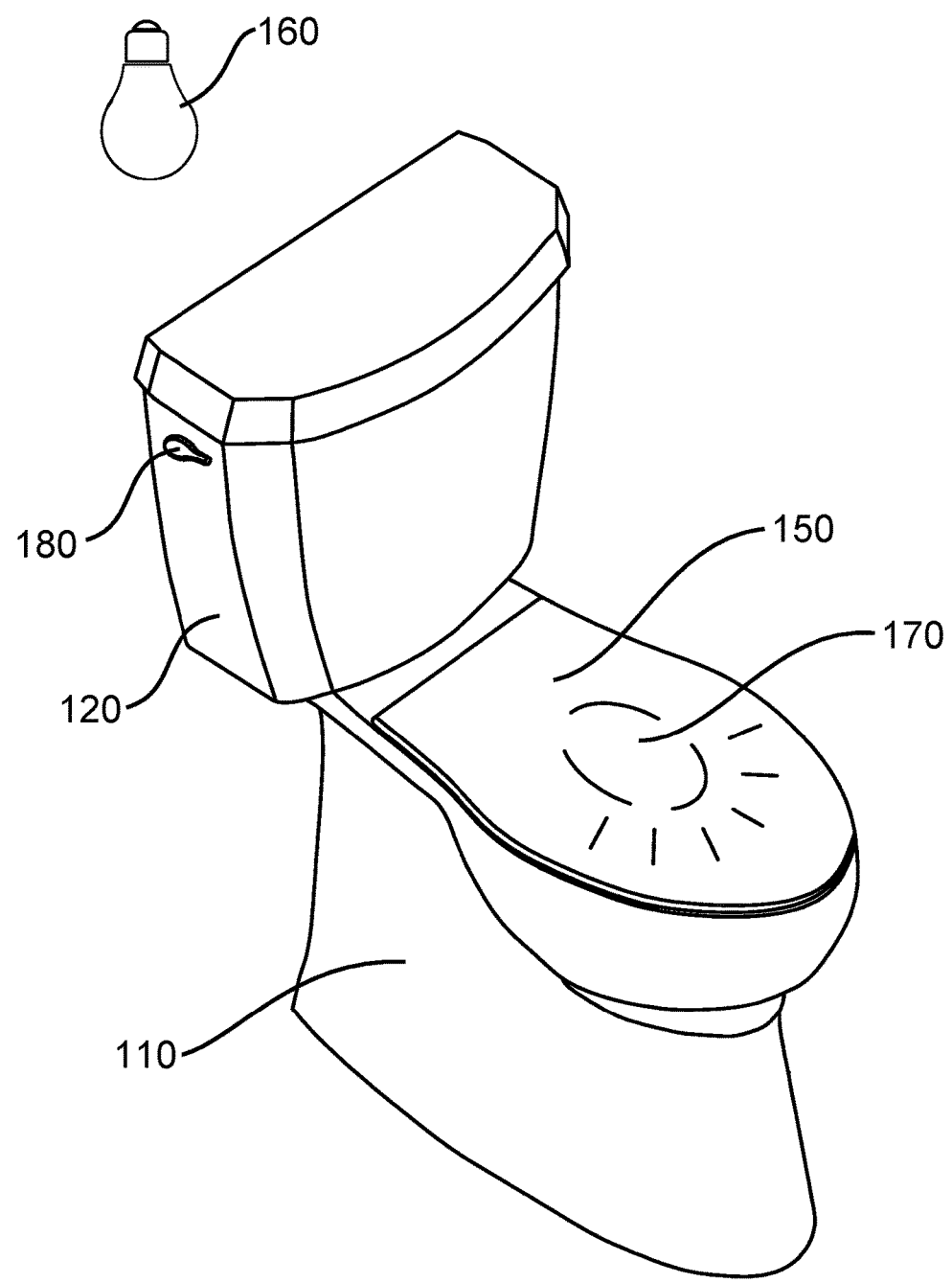
FIG. 4B is a perspective view of the toilet of FIG. 4A with the toilet lid lowered.

FIGS. 4A and 4B show yet another embodiment of the disclosed toilet in which UV light source 170 is positioned on or in toilet lid 150. In FIG. 4A, toilet lid 150 is in a raised position. When toilet lid 150 is in the raised position, UV light source 170 is not actuated and therefore, does not emit UV light. This may be the situation when the toilet is in use so as to avoid exposing the user or the non-doped titanium dioxide coated inner surface of toilet bowl 130 to UV light until it is desirable to disinfect the inner surface of toilet bowl 130. In contrast, visible light source 160 exposes the doped titanium dioxide coating on the outer shell of the toilet to visible light which activates the antimicrobial properties of this coating.

FIG. 4B shows toilet lid 150 in a lowered position. When toilet lid 150 is lowered, UV light source 170 is actuated and emits UV light toward the inner surface of toilet bowl 130. The antimicrobial properties of the non-doped titanium dioxide coating are then initiated to disinfect the inner surface of toilet bowl 130. Toilet lid 150 may be lowered and UV light source 170 actuated after the user has finished using the toilet and the user's excrement has exited toilet bowl 130, for example, through a flushing mechanism.

Figure 5:
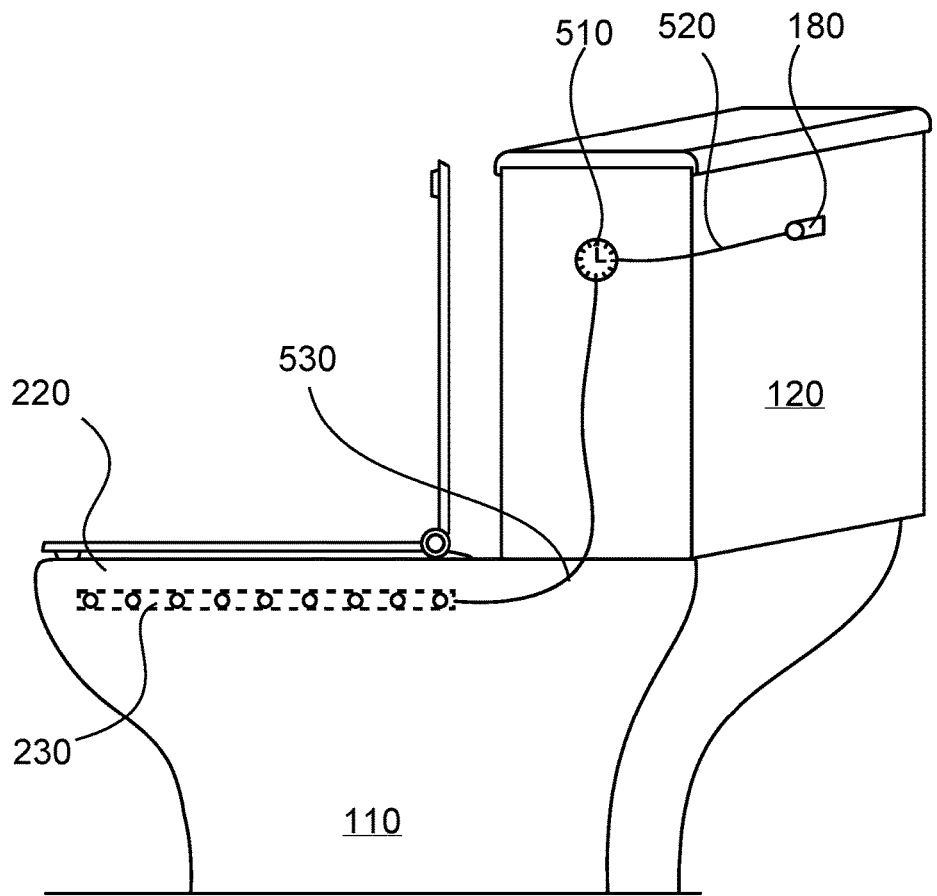
FIG. 5 is a side view of an embodiment of a titanium-dioxide coated toilet with the teachings and principles of the disclosure which includes a timing device, the timing device being in connection with the flush handle and the ultraviolet light source. An LED strip is on the inner surface of the toilet bowl

FIG. 5 shows an embodiment of the disclosed antimicrobial toilet in which the UV light source is LED strip 230 first presented in FIGS. 2A and 2B. The toilet includes flush handle 180 first presented in FIG. 1. In this embodiment, flush handle 180 is in electrical connection with timing device 510 through connection 520. Timing device 510 is also in electrical connection with LED strip 230 through connection 530. Timing device 510 may be calibrated to actuate LED strip 230 a defined number of seconds after flush handle 180 has been actuated. Consequently, the user may flush the toilet by actuating flush handle 180. This action is communicated to timing device 510 through connection 520. Timing device 510 then actuates LED strip 230 through connection 530 after a defined amount of time has passed. The defined amount of time between actuating flush handle 180 and actuating LED strip 230 may be the amount of time required for a typical toilet flush to be completed. Consequently, the user's excrement exits the toilet before LED strip 230 emits UV light to initiate the antimicrobial properties of the titanium dioxide coating on the inner surface of the toilet bowl.

It will be appreciated that, the embodiments in all of the drawings include a doped titanium dioxide coating on the outer shell of the toilet. A visible light source, which may illuminate the bathroom in which the toilet is placed, activates the antimicrobial properties of the doped titanium dioxide coating and disinfects the coated surfaces.

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that many changes may be made to the details of the above-described embodiments without departing from the underlying principles of the disclosure. The scope of the present disclosure should, therefore, be determined only by the following claims.

We claim:

1. An antimicrobial toilet, the antimicrobial toilet comprising:
a toilet bowl, the toilet bowl comprising:
an inner surface, the inner surface comprising a first coating, the first coating comprising non-doped titanium dioxide;
a rim, the rim encircling the toilet bowl; and
an ultraviolet light source comprising a plurality of light emitting diodes, wherein the plurality of light emitting diodes are disposed around the circumference of the inner surface of the toilet bowl below the rim of the toilet bowl;
an outer shell, the outer shell comprising a second coating, the second coating comprising doped titanium dioxide, wherein the doped titanium dioxide is antimicrobial in the presence of visible light.

2. The antimicrobial toilet of claim 1, wherein the second coating comprises nitrogen according to the following formula: $TiO_{2-x}N_x$.

3. The antimicrobial toilet of claim 1, wherein the second coating comprises between about 0.5% and about 2% nitrogen.

4. The antimicrobial toilet of claim 1, wherein the second coating comprises carbon according to the following formula: $C-TiO_2$.

5. The antimicrobial toilet of claim 1, wherein the second coating comprises carbon and nitrogen.

6. The antimicrobial toilet of claim 1, wherein the second coating comprises one or more of the following list: phosphorus, sulfur, and fluorine.

7. The antimicrobial toilet of claim 1, wherein the second coating comprises fluorine and nitrogen.

8. The antimicrobial toilet of claim 1, wherein the second coating comprises at least one noble metal.

9. The antimicrobial toilet of claim 8, wherein the at least one noble metal comprises silver.

10. The antimicrobial toilet of claim 1, wherein the second coating comprises at least one transition metal.

11. The antimicrobial toilet of claim 1, wherein the titanium dioxide in the coatings comprises anatase.

12. The antimicrobial toilet of claim 1, further comprising a switch, wherein the switch actuates the ultraviolet light source.

13. The antimicrobial toilet of claim 12, further comprising:
   a flush handle; and
   a timing device, wherein the flush handle is in electrical connection with the timing device, wherein actuation of the flush handle sends a first electrical signal to the timing device, and wherein the timing device is calibrated to send a second electrical signal to the ultraviolet light source a defined number of seconds after receiving the first electrical signal.

14. The antimicrobial toilet of claim 12, further comprising a toilet lid, wherein the switch is actuated when the toilet lid is in a lowered position, and wherein the switch is deactivated when the toilet lid is in a raised position.

15. The antimicrobial toilet of claim 1, wherein the titanium dioxide particles and the doped-titanium dioxide particles range in sizes of between 0.02 and 0.150 micrometers.

\* \* \* \* \*